United States Patent
Chang et al.

(10) Patent No.: US 6,938,211 B1
(45) Date of Patent: Aug. 30, 2005

(54) METHODS AND APPARATUS FOR AN IMAGE TRANSFER OBJECT

(75) Inventors: Paul Joseph Chang, Allison Park, PA (US); John C. Huffman, Menlo Park, CA (US); Benjamin J. McCurtain, San Francisco, CA (US); Jonathan Reis, Los Gatos, CA (US); Bradford V. Hebert, Piedmont, CA (US)

(73) Assignees: University of Pittsburgh of the Common Wealth System of Higher Education, Pittsburgh, PA (US); Stentor, Inc., Brisbane, CA (US)

( * ) Notice: Subject to any disclaimer, the term of this patent is extended or adjusted under 35 U.S.C. 154(b) by 769 days.

(21) Appl. No.: 09/449,015

(22) Filed: Nov. 24, 1999

(51) Int. Cl.[7] .................................................. G09G 5/00
(52) U.S. Cl. ...................... 715/733; 715/744; 715/748; 709/203
(58) Field of Search ................................ 345/424, 804, 345/744, 748, 751, 752, 760, 733; 709/203, 219

(56) References Cited

U.S. PATENT DOCUMENTS

| | | | |
|---|---|---|---|
| 5,606,707 A | * 2/1997 | Tomassi et al. ............ | 345/418 |
| 5,790,793 A | 8/1998 | Higley | |
| 5,803,914 A | * 9/1998 | Ryals et al. ................. | 600/407 |
| 5,822,544 A | * 10/1998 | Chaco et al. ................. | 705/2 |
| 5,838,906 A | 11/1998 | Doyle et al. | |
| 5,864,366 A | 1/1999 | Yeo | |
| 5,877,819 A | * 3/1999 | Branson ..................... | 348/701 |
| 5,954,650 A | * 9/1999 | Saito et al. .................. | 600/425 |
| 5,986,662 A | 11/1999 | Argiro et al. | |
| 6,006,231 A | * 12/1999 | Popa .......................... | 707/101 |
| 6,011,537 A | * 1/2000 | Slotznick .................... | 345/733 |
| 6,081,267 A | * 6/2000 | Stockham et al. ........... | 345/788 |
| 6,137,527 A | * 10/2000 | Abdel-Malek et al. ....... | 348/77 |
| 6,260,021 B1 | * 7/2001 | Wong et al. .................. | 705/2 |

* cited by examiner

*Primary Examiner*—Raymond J. Bayerl
*Assistant Examiner*—Cuong T. Thai

(57) ABSTRACT

An image transfer object is disclosed that provides the necessary mechanism to conduct a dynamic transfer operation. The image transfer object includes a static reference to dynamic data. The image data is "dynamic", in that the user may request additional views of the image. An image recipient computer receives the static reference to identify a source image on a server, and generates a first request, based on the static reference, for a view of the source image to the server. In response, the server transmits data to the image recipient computer. The image recipient computer displays the first view of the source image for viewing by the user. The user may then select a different portion of the source image, and/or a different resolution to designate a second view of the source image. The image recipient computer generates a second request to the image server for the second view, and the image server transmits additional data to generate the second view of the source image. Thereafter, the second view of the source image is displayed at the image recipient computer. A sender of the image may transmit a context for the image via e-mail or the recipient computer may download the image from a Web site. Techniques to configure the dynamic transfer object are also disclosed.

19 Claims, 11 Drawing Sheets

Hierarchical Data Structure

Hierarchical Data Structure

METHODS AND APPARATUS FOR AN IMAGE TRANSFER OBJECT

BACKGROUND OF THE INVENTION

1. Field of the Invention

The present invention is directed toward the field of transferring, browsing and viewing images, and more specifically to an image object that permits fast, efficient transfer, manipulation and viewing of large images.

2. Art Background

The Internet provides opportunities to transmit information quickly, reliably, and efficiently. For example, the Internet is a good medium to transmit email messages consisting of a size less than a few kilobytes of data. Email is also commonly used to transmit data files, typically attached to the email messages. For example, it is common to attach files, such as word processing documents, that consist of a several kilobytes of data. With increased advancements in video and imaging technology, there is an increased demand to transmit large files. For example, it is common for Internet users to transmit digitized images generated from pictures. In the scientific and medical community, it is desirable to transmit large image files. These image files may comprise detailed maps, image data collected from sensors, medical images, etc.

In the medical imaging application, it has become more common for images to be stored, distributed, and viewed in digital form using computer technology. Currently, Picture Archival and Communication Systems or PACS have been in widespread use. In a typical PACS application, image data obtained by imaging equipment such as CT scanners or MRI scanners are stored in the form of computer data files. The size of a data file for an image varies depending on the size and resolution of the image. For example, a typical image file for a diagnostic-quality chest X-ray is on the order of 10 megabytes (MB). The image data files are usually formatted in a "standard" or widely accepted format. In the medical field, one widely used image format is known as DICOM. The DICOM image data files are distributed over computer networks to specialized viewing stations capable of converting the image data to high-resolution images on a CRT display.

Although the Internet is a good medium for transmitting small files, when transferring large images, such as large image files, which may comprise files of over 10 megabytes of data, the Internet becomes slow. For example, currently, many computer users, particularly home users, only have 56 kilobit per second ("56K") modems to transmit data across the Internet. Even higher bandwidth connections to the Internet, which permits faster transmission of data, do not accommodate the ability to transmit extremely large data files. Accordingly, it is desirable to develop a system that permits users to communicate images over networks, including the Internet, without having to email large data files. It is also desirable to develop a system that permits users to manipulate those images as dynamic images.

SUMMARY OF THE INVENTION

An image transfer object provides the necessary mechanism to conduct a dynamic transfer operation. At a minimum, the image transfer object includes a static reference to dynamic data, such as image data. An image recipient computer receives the static reference to identify one or more source images on a server. To initiate the dynamic transfer operation, the image recipient computer generates a first request, based on the static reference, for a view of the source image(s) to the server. In response, the server transmits data to the image recipient computer. The image recipient computer displays the first view of the source image for viewing by the user. The image data is "dynamic", in that the user may request additional views of the image. To accomplish this, the user selects a different portion of the source image, and/or a different resolution to designate a second view of the source image. The image recipient computer generates a second request to the image server for the second view, and the image server transmits additional data to generate the second view of the source image. Thereafter, the second view of the source image is displayed at the image recipient computer.

A sender of the image may transmit a context for the image (i.e., an initial view) to the recipient through any means. In one embodiment, the sender transmits the static reference and image transfer object to a recipient computer via e-mail. In other embodiments, the recipient computer receives the static reference and image transfer object by downloading the static reference from a Web site.

In one embodiment, the image transfer object also determines if any additional software components are necessary to conduct the dynamic image transfer operation. If additional software components are necessary, a server transfers the additional software components to conduct the dynamic image transfer.

BRIEF DESCRIPTION OF THE DRAWINGS

FIG. 6b illustrates level three and level four decompositions for the 4K×4K source image of FIG. 6a.

DETAILED DESCRIPTION

The present invention provides a mechanism to transmit a static reference to dynamic data. In one embodiment, the dynamic data consists of image data. For this embodiment, the image transfer object permits a user to browse the image to obtain different views (i.e., view different portions of the image and view the image at different resolutions). Although the image transfer object is described herein for use in viewing images, any type of data may used without departing from the spirit and scope of the invention. The image transfer object encapsulates both the functionality to view an image (i.e., the viewer) and the static reference to an image. As described more fully below, the recipient of an image: receives an image transfer object; configures a dynamic image operation through use of the image transfer object; receives an initial view of the image; and browses the image to obtain different views.

Figure 1:
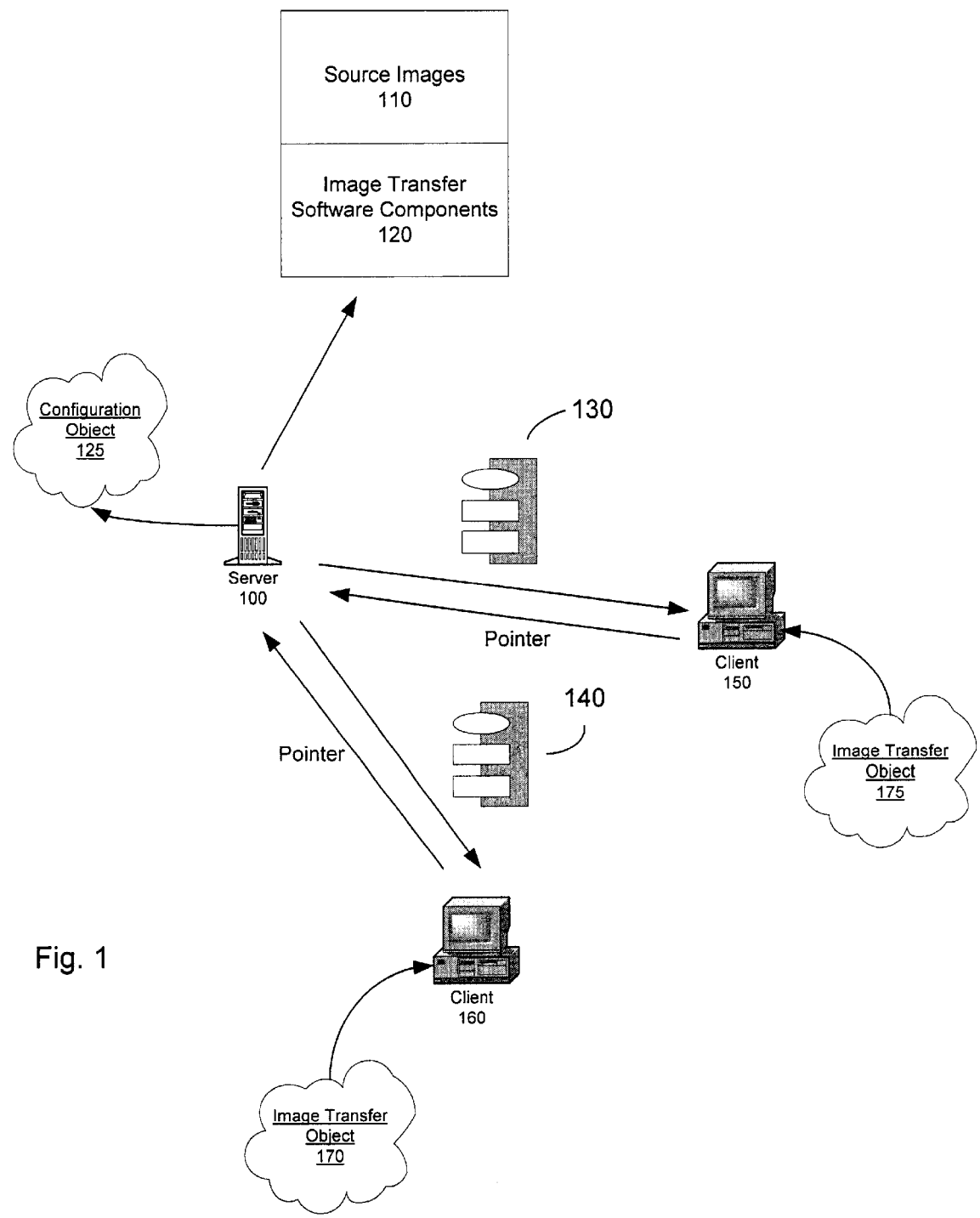
FIG. 1 illustrates one embodiment for configuring the image transfer object of the present invention at a client.

Configuration of the Image Transfer Object:

FIG. 1 illustrates one embodiment for configuring the image transfer object of the present invention at a client. A shown in FIG. 1, a server 100 stores or accesses a plurality of source images 110 and image transfer software components 120. The source images 110 comprise any type of image for use with the dynamic image transfer operations of the present invention. The image transfer software components 120 comprise software modules necessary to conduct the dynamic image transfer of source images 110.

The diagram of FIG. 1 shows a network configuration between client(s) (i.e., clients 150 and 160) and a server (i.e., server 100). Clients 150 and 160 receive an image transfer object. In general, the image transfer object (e.g., 170 or 175) encapsulates data, also referred to as properties, and operations or methods. In one embodiment, the image transfer object includes, as properties, an identification to configuration software (e.g., configuration object 125 in FIG. 1), an identification to source image(s), as well as an identification to an initial view of the source image. In one embodiment, the image transfer object includes, as methods or properties, software to conduct a dynamic image transfer process, software to configure executable software at the client to conduct the dynamic image transfer operation, or software to initiate the process to configure executable software at the client to conduct the dynamic image transfer operation. As described more fully below, the dynamic image transfer operations permit the client to request at least portions of the source image at desired resolutions.

First, the client receives at least a minimal image transfer object. Some embodiments for receiving the image transfer object at the client are discussed below in conjunction with FIGS. 4a, 4b, 4c and 4d. In one embodiment, the client receives a "seed", to invoke processes on a server to configure software at the client. As shown in FIG. 1, server 100 includes a configuration object 125. In general, configuration object 125 installs software, in conjunction with the image transfer object, to permit the client to conduct the dynamic image transfer operations. For this embodiment, the client receives, as part of the image transfer object, a "pointer" to invoke a process at a server. For an embodiment that uses CORBA services for the dynamic image transfer operations, the client passes an interoperative object reference ("IOR") to invoke the server process (e.g., configuration object 125). With this pointer, the client (e.g., client 150 or 160, FIG. 1) establishes a proxy connection with the server (e.g., server 100, FIG. 1), and invokes a process on the server (e.g., configuration object 125) to fully configure executable software at the client. For example, the client may generate a remote procedure call ("RPC") to invoke the process at the server. The client—server may utilize any protocol for this initial connection. For example, the client—server may communicate via a hypertext transfer protocol ("http"), socket services, common object request broker architecture ("CORBA") communication services, etc. However, implementing the initial protocol with "http" encompasses a broad installed computer base that supports http transfers.

For this embodiment, the server process (e.g., configuration object 125) interrogates the client (e.g., clients 150 and 160) to ascertain whether the client possess the requisite resources to execute the dynamic image transfer operations. For example, in one embodiment for implementing the dynamic transfer operation, the image transfer object utilizes services from the Common Object Request Broker Architecture ("CORBA"). For this embodiment, the image transfer object determines whether the necessary CORBA components are available at the client. If additional software components are necessary, the server transmits the software components to the client. Each client may require different software components, depending upon software installed at the client. For the embodiment of the image transfer object that utilizes services from the CORBA, client 150 may process the necessary CORBA components, whereas client 160 may not. This is illustrated in FIG. 1 by server 100 transmitting software components 130 to client 150 and software components 140 to client 160 (i.e., different software components). The client—server communication may utilize any protocol to transfer to the software components, including file transfer protocol ("FTP"), http, socket services or CORBA services.

In other embodiments, the image transfer object includes the functionality for the client (e.g., clients 150 and 160) to determine whether any software components are necessary to fully configure the dynamic image transfer operations. If additional software components are necessary, the client (e.g., clients 150 and 160) queries the server (e.g., server 100), through generation of a proxy connection, to receive the necessary software components. As described above, any software protocol may be used to transfer the software components, such as the file transfer protocol ("FTP").

In one embodiment, the image transfer object comprises instance data to conduct the dynamic image transfer operation for a specific image and to identify a specific view within the image. To accomplish these functions, the image transfer object includes a unique identification ("UID") to identify one or more source images on the server. In one embodiment, the UID identifies a collection of images. For this embodiment, additional instance data is included to identify a source image within the collection of source images. In a medical informatics application, described below, the collection of source images comprises medical images (i.e., images and series) for a patient study.

The initial view of the source image identified in the image transfer object is expressed as a "request." As used herein, the "view" of the source image connotes both the part of the source image (i.e., either the entire source image or a part) and the resolution of the source image. As described more fully below, the request comprises a set of coefficient coordinates, which map to pixel coordinates for display on the client, necessary to reconstruct the view of the source image. Furthermore, the image transfer object comprises, as instance data, the pointer (e.g., IOR) to identify the configuration object on the server (i.e., configuration object 125 on server 100 (FIG. 1)). Furthermore, the server used to configure the object may be a different server than the server that stores the image(s). For this embodiment, the instance data also identifies a network address for the image server.

In one embodiment, the dynamic image transfer operation comprises, in part, executable software configured as a Microsoft® ActiveX Control. For this embodiment, the ActiveX Control is a "plug-in" to a Web browser application. Specifically, the ActiveX Control implements, for the dynamic image transfer operation, a user interface (within the browser application), server requests based on user selection of source image views, and image reconstruction at the client. One embodiment for implementing a user interface for the dynamic image transfer operation is described in U.S. patent application Ser. No. 09/449,115 entitled "User Interface for a Medical Informatics System", inventors, Paul Joseph Chang M. D., Bradford V. Hebert, and Ben McCurtain, filed concurrently herewith [Express Mail Label No.: EL497530676US], and is expressly incorporated herein by reference. As part of the configuration processes, the client possess or receives from the server the resources necessary to activate an ActiveX Control as an executable plug-in to a web browser application. The client either receives the ActiveX Control executable, as part of the image transfer object, or downloads the ActiveX Control executable from the server.

In one embodiment, the dynamic image transfer operation utilizes communication resources of the Common Object Request Broker Architecture ("CORBA"). For this embodiment, a client generates an event, and the server 100 subscribes to that event. However, any communication mechanism to setup communications among multiple computers on a network may be used. For example, the server—clients may use socket services provided through Unix based operating systems. After configuration of the image transfer object at the client, the client possesses the necessary components to conduct the dynamic image transfer operation.

Figure 2A:
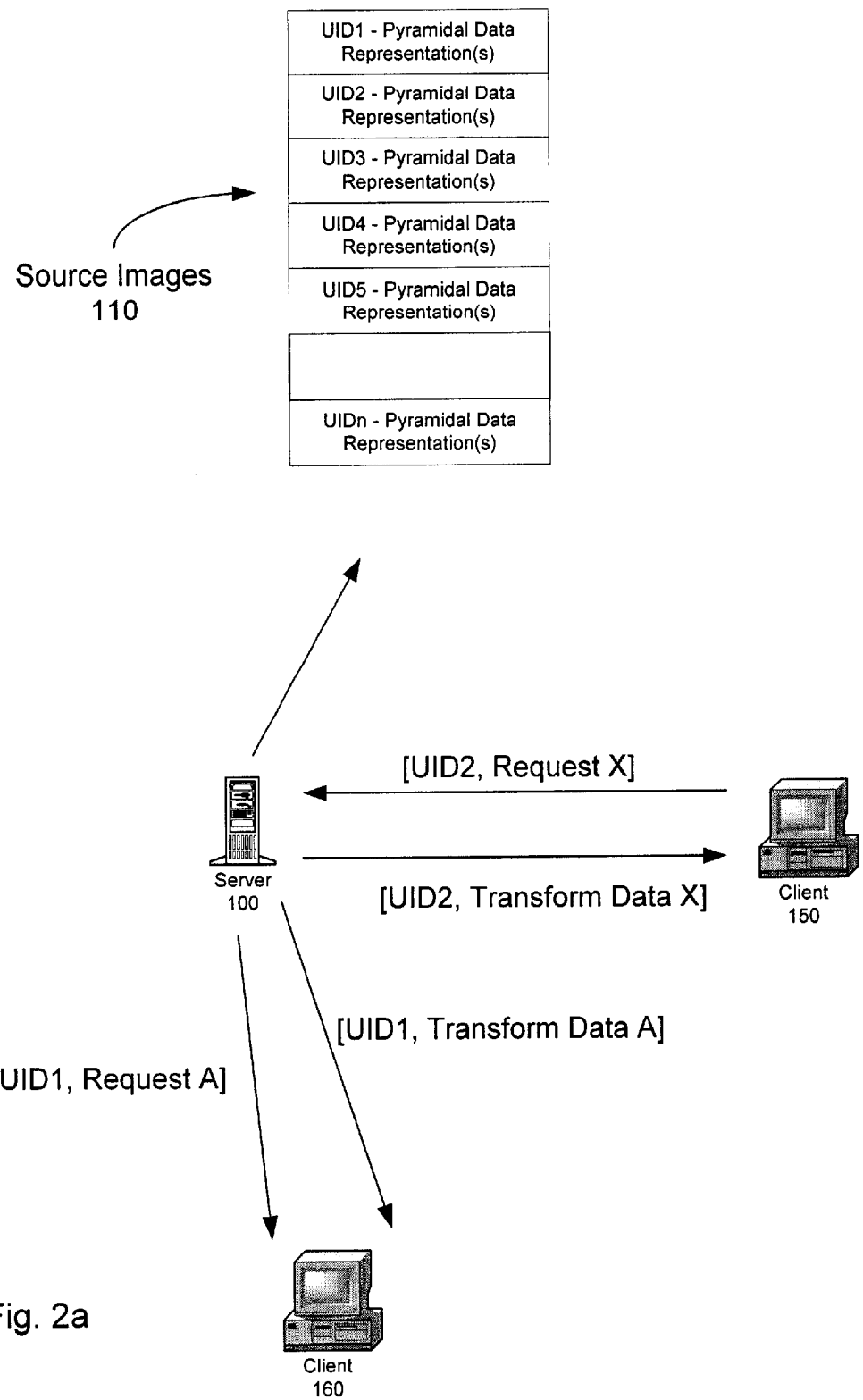
FIG. 2a illustrates one embodiment for dynamic image transfer utilizing the image transfer object of the present invention.

FIG. 2*a* illustrates one embodiment for dynamic image transfer utilizing the image transfer object of the present invention. FIG. 2*a* shows a plurality of pyramidal data images accessible by server 100. As described more fully below in conjunction with FIGS. 5 and 6, the source images 110 are decomposed into one ore more hierarchical or pyramidal data representations. In one embodiment, the pyramidal data representations of source images 110 consist of transform data sufficient to reconstruct the source image, or portions thereof, at various resolutions. The image transfer object has applications for use in medical informatics. For this application, source images 110 constitute digitized medical images, decomposed into the hierarchical representation. As shown in FIG. 2*a*, each pyramidal data image is identified by a unique identification number ("UID"), so as to uniquely identify the image in the server.

For the example of FIG. 2*a*, client 160 received, as part of the image transfer object 170, an identification of pyramidal data representation 1 (i.e., UID1). Also, for this example, client 150 received, as part of the image transfer object 175, an identification of pyramidal data representation 2 (i.e., UID2). The image transfer object on client 160 generates a request to server 100 to obtain a view of the source image identified in the image transfer object. Specifically, for this embodiment, the client 160 generates a request to server 100 to obtain transform data sufficient to reconstruct this view at the client 160. This operation is illustrated in FIG. 2*a* by the illustration of the client transmitting "Request A" for image UID1, and the server 100 transferring "Transform Data A" for image UID1. Similarly, client 150 obtains its view of UID2 source image by generating "Request X" for pyramidal data representation UID2, and the server 100 transferring "Transform Data X." Transform Data X comprises data necessary to reconstruct the view at client 150.

The image transfer object of the present invention permits the image recipient to receive a "view" of an image selected by the image sender. However, this view is not a static image, but a dynamic image. After viewing the initial view, the client may generate requests to receive different views of the image (i.e., receive different portions of the source image and/or view the source image at different resolutions). This provides a truly dynamic environment, whereby the image recipient only receives an initial "pointer" to the first view, and the image recipient may then traverse the source image to view as many different views of the source image as desired.

Figure 2B:
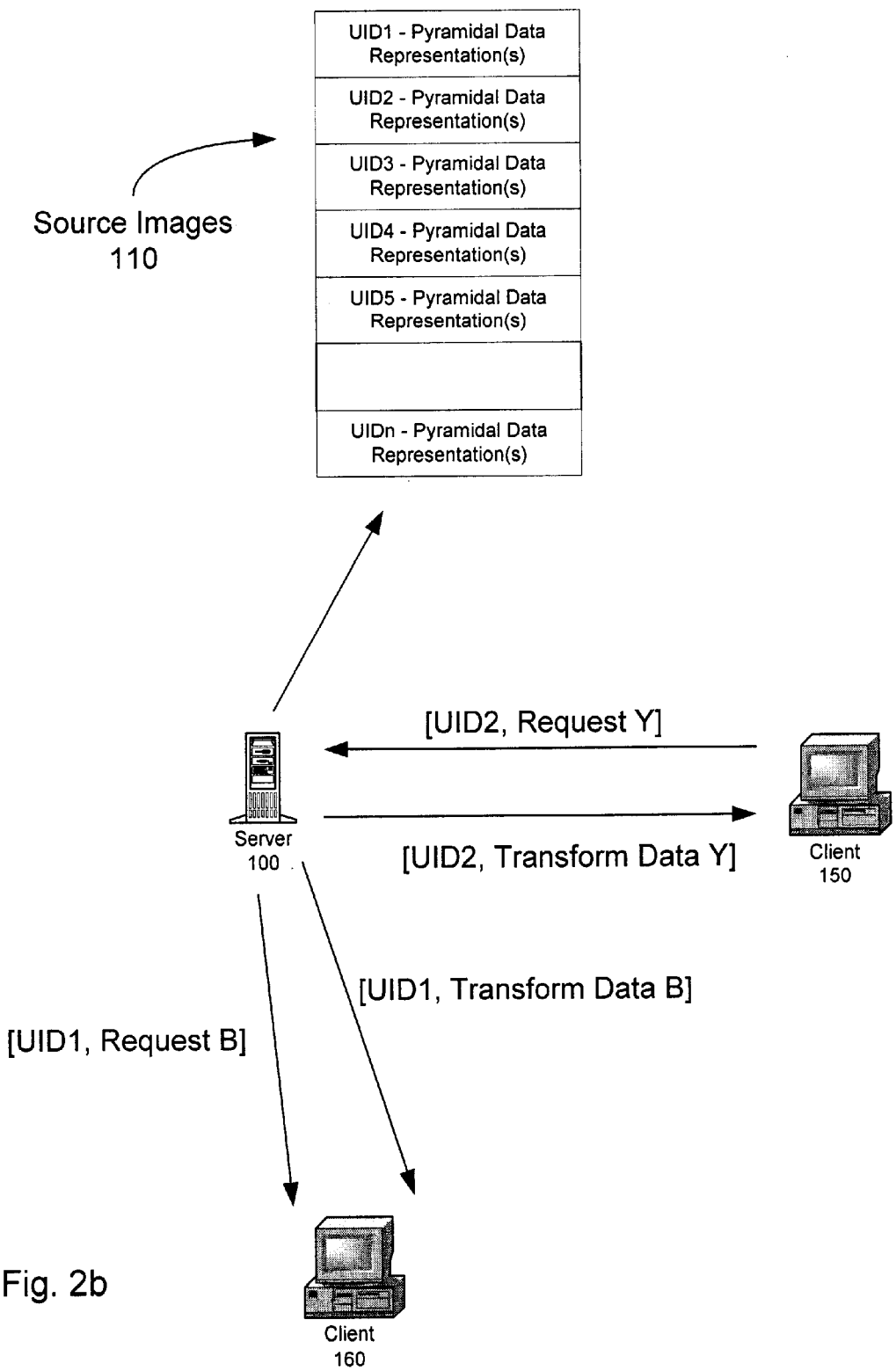
FIG. 2b illustrates a second dynamic transfer operation for the example of FIG. 2a to view a different portion of the source image.

FIG. 2*b* illustrates a second dynamic transfer operation for the example of FIG. 2*a* to view a different portion of the source image. Specifically, for this example, client 160 generates "Request B", a different request than "Request A", to receive a second view of source image 1 (i.e., UID1). In turn, server 100 transmits "Transform Data B" to client 160 to permit reconstruction of the second view of the source image at client 160. Similarly, for this example, client 150 generates a request for a second view of UID 2, "Request Y", and receives, from server 100, "Transform Data Y."

Figure 3:
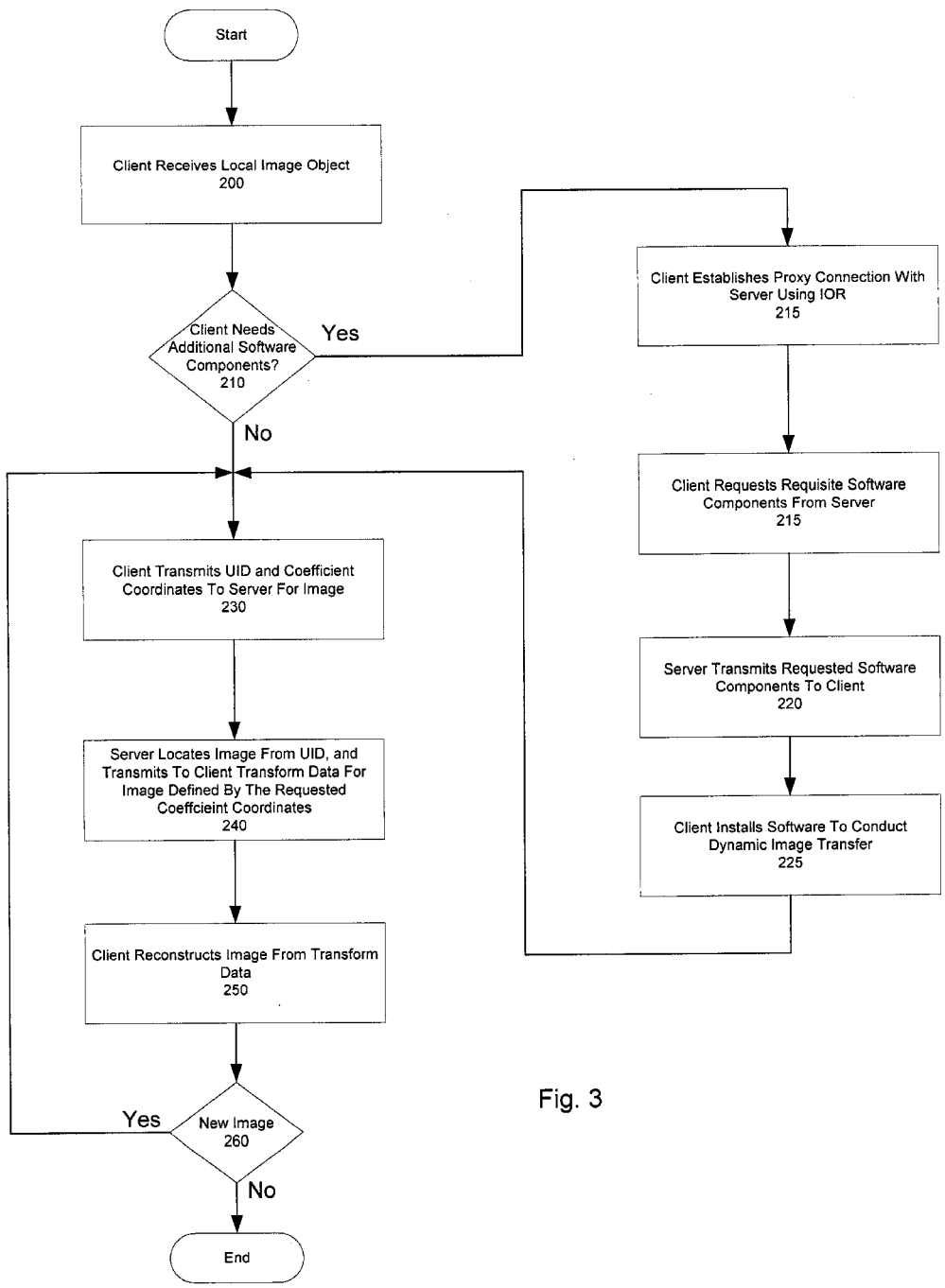
FIG. 3 is a flow diagram illustrating one embodiment for dynamic image transfer utilizing the image transfer object of the present invention.

FIG. 3 is a flow diagram illustrating one embodiment for dynamic image transfer utilizing the image transfer object of the present invention. The client receives a local image object (block 200, FIG. 3). The "local" image object contains, at a minimum, the necessary data to identify a source image, an initial view of the source image, methods for implementing the dynamic image transfer operation, as well as methods to obtain the necessary software components to fully install the image transfer object. The client, through the image transfer object, determines whether the client possesses the requisite resources to execute the image transfer object. For example, in one embodiment, the image transfer object is implemented as an ActiveX control. For this embodiment, the client computer requires software to run the image transfer object as an ActiveX "plug-in" component. Also, in one embodiment, the image transfer object implements CORBA services to establish communications between the client and server to conduct the dynamic image transfer. For this embodiment, the client ascertains whether it has the requisite CORBA services to implement the communications protocol. If the client does not require additional software components, then the image transfer object may be installed at the client for operation of the dynamic image transfer process. If the client needs additional software components, then the client establishes a proxy connection with the server (blocks 210 and 215, FIG. 3). The client establishes a proxy connection with the server using the interoperative object reference ("IOR") to identify the configuration object 125 (FIG. 1) on the server 100. Through this dialogue, the client requests the requisite software components from the server (block 215, FIG. 3). The server then transmits the requested software components to the client (block 220, FIG. 3). Upon receipt, the client installs the software components, and thus possesses the requisite resources to conduct the dynamic image transfer (block 225, FIG. 3).

From the encapsulated data, the image transfer object 170 transmits, to the server, a request for the view, consisting of the UID (e.g., including an identification of a source image for a collection of source images)) and a set of coefficient coordinates (block 230, FIG. 3). From the request, the server locates the image from the UID, and transmits transform data to the client for the view of the source image defined by the coefficient coordinates of the request (block 240, FIG. 3). With the transform data, the client reconstructs the view of the source image (block 250, FIG. 3). If the image recipient desires to view another view of the source image, then a new request at the image recipient computer is generated, transform data is transferred, and a new view is reconstructed at the client recipient computer (blocks 260, 230, 240 and 250, FIG. 3).

Figure 4A:
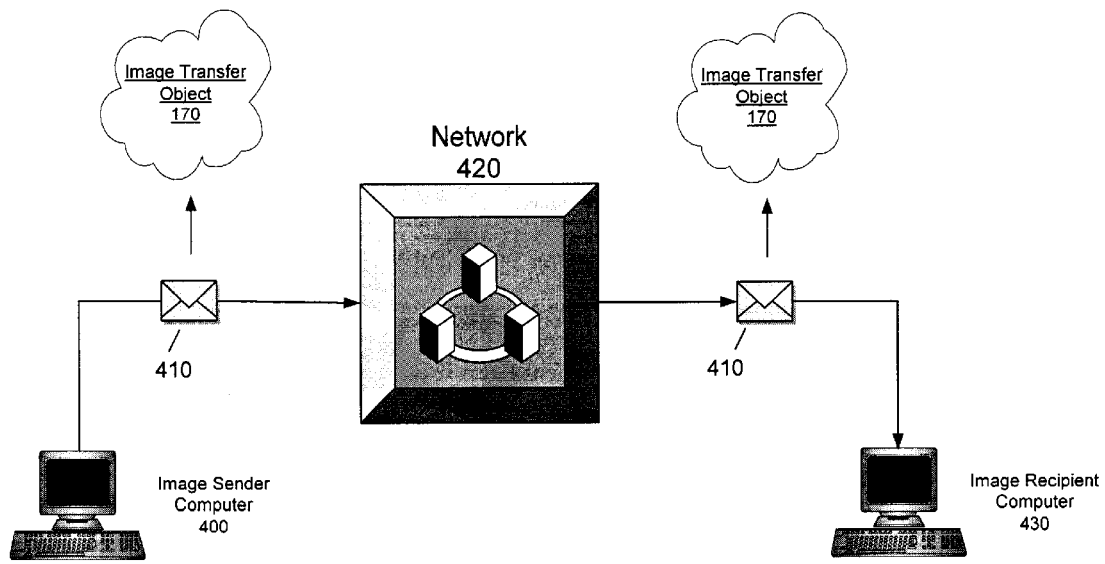
FIG. 4a illustrates one embodiment for communicating an image and view to an image recipient.

Sending the Image Transfer Object:

FIG. 4a illustrates one embodiment for communicating an image and view to an image recipient. For this embodiment, an image sender computer 400 generates an image transfer object 170, and attaches the image transfer object 170 to email message 410. The email message 410, with the image transfer object 170 attachment, is transmitted over a network to the image recipient computer 430. The network 420 may comprise a public packet based network (i.e., IP), such as the Internet, a public switching telephone network ("PSTN") or any private local area or wide area network. Thus, for the embodiment of FIG. 4a, the image recipient computer 430 receives the image transfer object 170 via email.

Figure 4B:
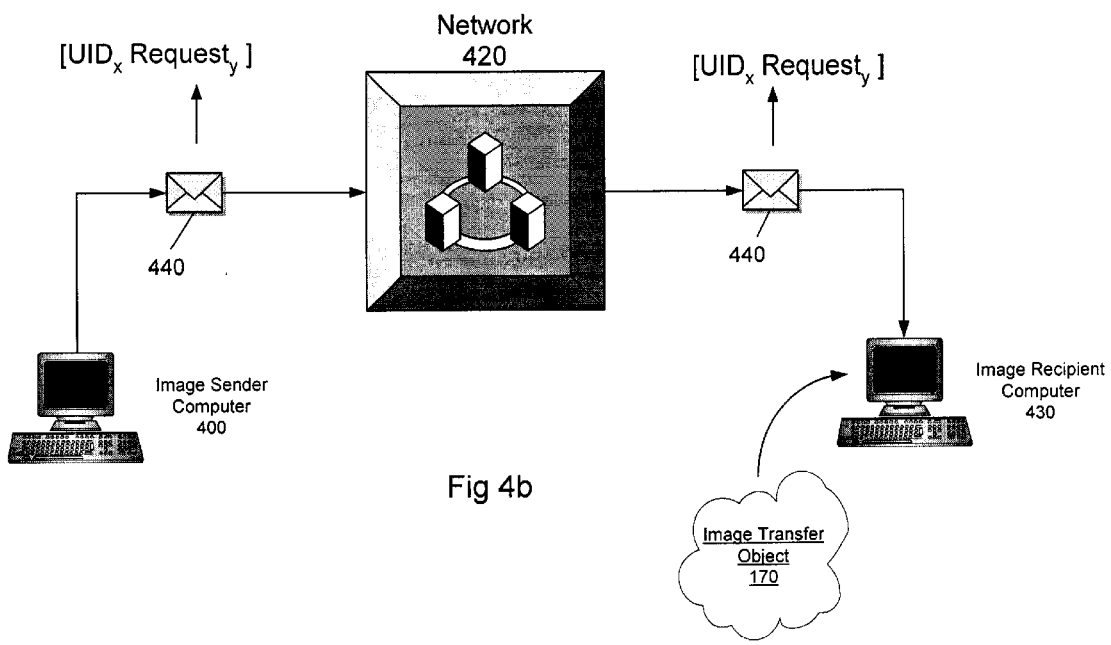
FIG. 4b illustrates another embodiment for communicating an image to an image recipient computer.

FIG. 4b illustrates another embodiment for communicating an image to a image recipient computer. In this example, image recipient computer 430 already comprises the image transfer object 170. The image sender, aware that the image recipient computer 430 may execute the dynamic transfer image process, transmits an email 440. As shown in FIG. 4b, the email 440 includes an identification to a source image and a view of that source image. Specifically, for this embodiment, the email 440 includes a UID, which identifies source image(s) at the server, and a dynamic image transfer request. The dynamic image transfer requests contain a set of coefficient coordinates necessary to reconstruct the desired image at the image recipient computer. Email 440 may be transmitted through any type of network, including a public switched telephone network ("PSTN") or a packet based network (IP), either public or private.

Figure 4C:
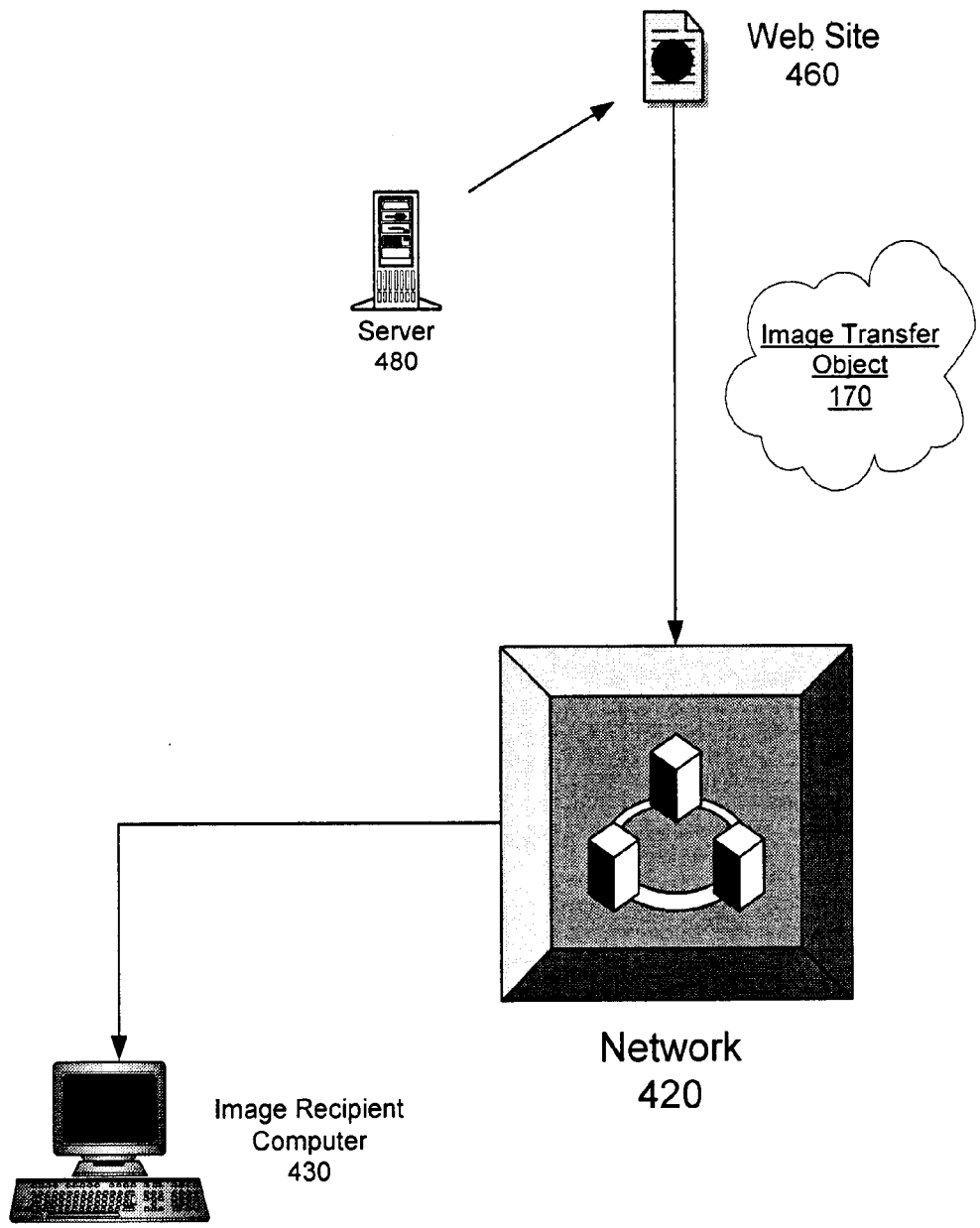
FIG. 4c illustrates a third embodiment for transferring the image transfer object of the present invention to a client computer.

FIG. 4c illustrates a third embodiment for transferring the image transfer object of the present invention to a client computer. For this embodiment, a client computer (i.e., image recipient computer 430), using web (i.e., Internet) browser software, goes to an Internet Website or other network location. FIG. 4c shows that a server 480 supports a Web Site 460. The server 480 may be independent of the image server used to transfer image data to the client. Alternatively, the servers may operate in conjunction with one another. For this embodiment, the image transfer object 170 is downloaded from the Web Site to the image recipient computer 430. Again, any type of network may be used to access the network location (e.g., Web Site).

Figure 4D:
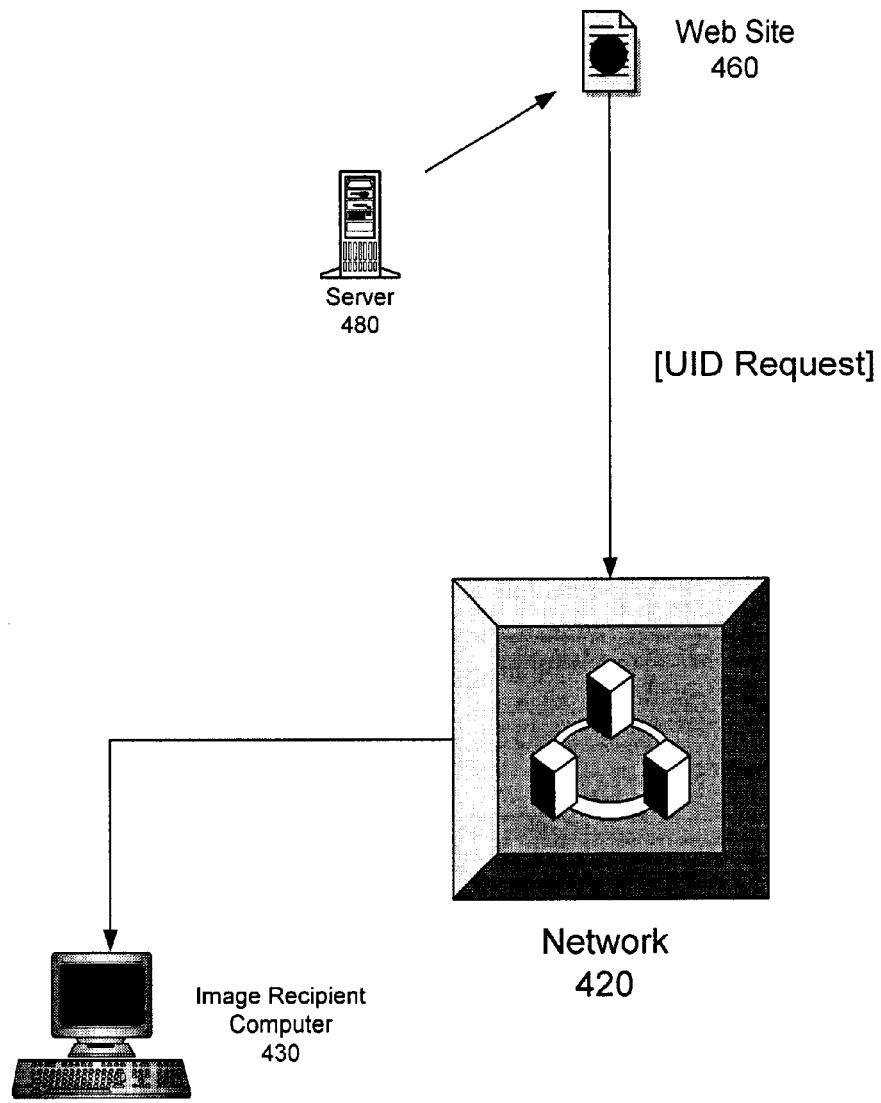
FIG. 4d illustrates another embodiment for communicating an image to a recipient computer.

FIG. 4d illustrates another embodiment for communicating an image to a recipient computer. For this embodiment, the image recipient computer 430 already has access to the image transfer object 170 to execute the dynamic image transfer process. An identification to a source image and a view within the source image is stored on Web Site 460. The user at the image recipient computer 430 downloads the source image and view information. This is illustrated in FIG. 4d through the transfer of [UID, Request] from a Web Site 460 to image recipient computer 430. This technique has applications for both public and private networks. For example, a real estate based Web Site may contain photographic images of properties offered for sale. Through the embodiments of FIGS. 4c and 4d, a user, through a web browser, may select images (e.g., photographs of a desired property), and through the image transfer object, view desired views of the selected image. Accordingly, this permits integration of the dynamic image transfer system into a standard Web application.

Security and Validation:

In one embodiment, the image transfer object of the present invention implements access control to images. For this embodiment, the data encapsulated in the image transfer object (e.g., pointer to configuration object, UID of image, and view of image) are sent in the clear. Thus, no additional processing is required at the image sender computer to encrypt the image transfer object, and no additional processing is required at the image recipient computer to decrypt the image transfer object. Instead, access control is conducted at the image server. Specifically, in one embodiment, when the image recipient computer requests to view the image, the image server requires a login procedure from the image recipient. Access control at the image server may be implemented in any manner.

The image server access control system may involve multiple levels of security. For example, as a first level of security, the access control system at the image server validates the user as a user with access rights to the image server. This function may be implemented through a well-known user login procedure; wherein, the user submits a name and password, and the access control system determines whether the user—password combination is valid. As a second level of security, an access control mechanism is implemented at the image level. In one embodiment, the image recipient computer submits to the image server, to view an image, the image UID. The access control system then determines whether the user is authorized to view that image. This level of security may be implemented similar to a file access control system on file servers. As a third level of security, an access control mechanism is implemented at the view level. For example, an image may contain non-secure information when viewed at a low resolution, but the image may contain secure information when viewed at a higher resolution. Thus, access control may be implemented to permit a user to obtain only selected views of the image.

Figure 5:
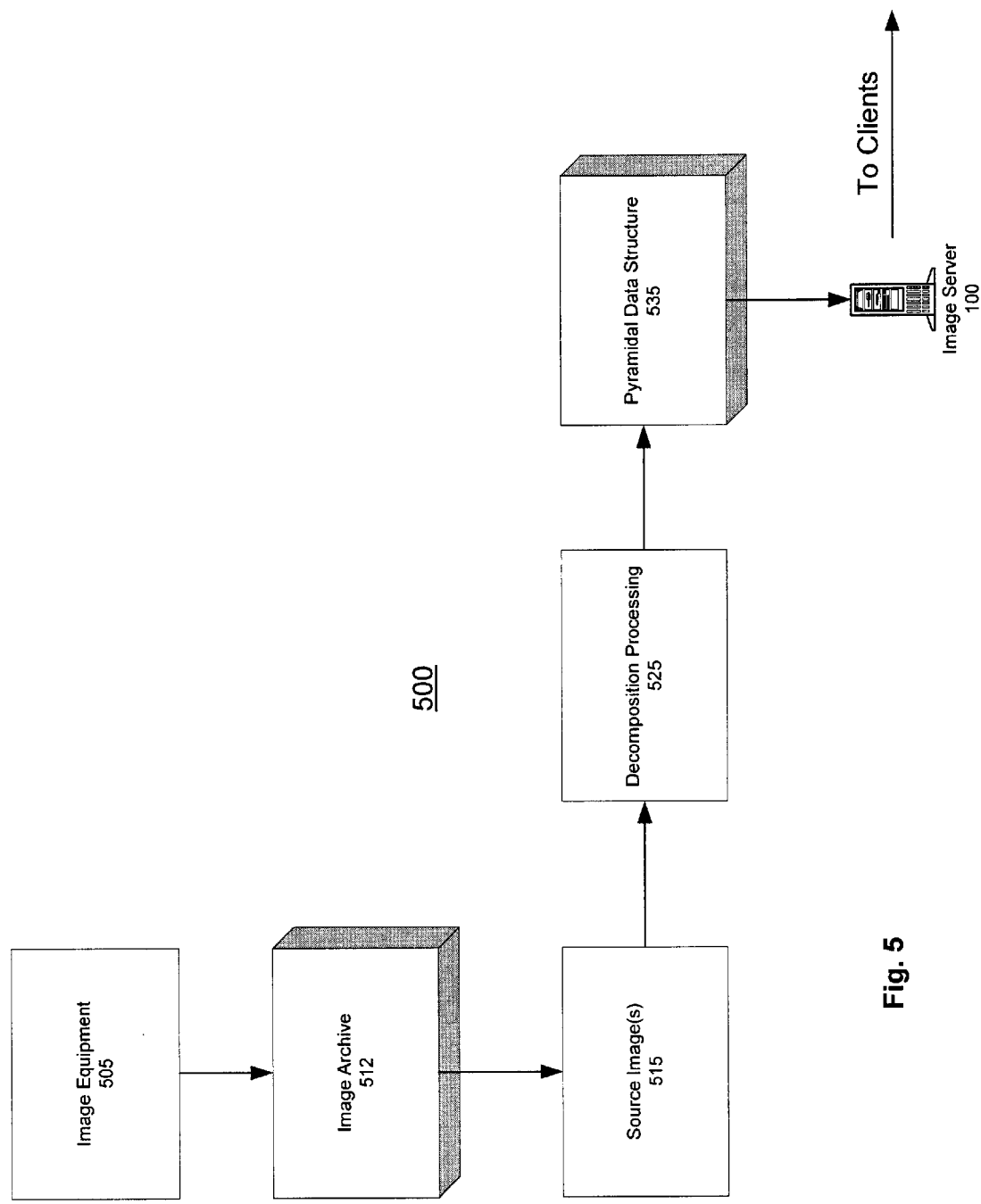
FIG. 5 illustrates one embodiment for processing source images for use with the image transfer object of the present invention.

Dynamic Image Transfer System:

FIG. 5 illustrates one embodiment for processing source images for use with the image transfer object of the present invention. In one embodiment, the dynamic image transfer system is part of a medical informatics system. For this embodiment, a medical informatics system 500 includes imaging equipment 505 to generate source images 515 for storage in electronic form in an image archive 512. The image archive 512 contains electronic storage components such as disk drives and tape drives used to store the images in a highly reliable manner. The images are stored in a suitable archival format, such as the DICOM format. The imaging equipment 505 includes any type of equipment to generate images, including medical equipment (e.g., X-ray equipment, CT scanners, and MR scanners).

For non-medical informatics applications, the dynamic image transfer system receives, as input, source images 515, and generates, as an output, pyramidal data structure 535. The dynamic image transfer system 500 includes at least one image server 100. The pyramidal data structure 535 is stored in image server 100. Image server 100 is coupled to one or more client computers via a direct or network connection (See FIGS. 1, 2a and 2b).

In one embodiment, the image server 100 transmits to the client computers (e.g., 150 and 160) transformations of the source image 515 ("transform data"), stored as pyramidal data structure 535, to re-create images and sub-images in the client computers. The image server 100 transfers only the coefficient data required to reconstruct a requested image at the client(s), thus implementing a "just in time" data delivery system. The dynamic image transfer operation permits the use of a network with moderate bandwidth capacity, while still providing low latency for transfer of large data files from the image server 100 to client computers (e.g., clients 150 and 160, FIG. 1). For example, the network for the dynamic image transfer system may utilize an Ethernet (10baseT) medium or an ISDN transmission medium. Regardless, any network, including wide area networks (WANs) and local area networks (LANs) may be used without deviating from the spirit and scope of the invention.

For the medical informatics application, the medical informatics system 500 processes one or more source images 515. Generally, the source image(s) 515 includes a digitized medical image generated from medical instrumentation (e.g., mammogram, X-Ray, MRI, CATSCAN, etc.).

As shown in FIG. 5, the source image(s) 515, whether medical images or other types of images, are input to decomposition processing 525. In general, decomposition processing 525 transforms the source images 515 into the pyramidal data structure 535. In general, the pyramidal data structure 535 comprises a hierarchical representation of the source image. Each level of the hierarchical representation is sufficient to reconstruct the source image at a given resolution. In one embodiment, the decomposition processing 525 utilizes a sub-band decomposition to generate the hierarchical representation. In general, sub-band decomposition consists of executing a process to separate "high-pass" information from "low-pass" information. For the sub-band decomposition embodiment, decomposition processing 525 comprises a finite impulse response (FIR) filter.

In one embodiment that uses sub-band decomposition, the decomposition processing 525 uses wavelet transforms, which are a sub-class of the sub-band decomposition transform. In general, the wavelet transform may be selected so that the kernels aggregate a sufficient amount of the image information into the terms or coefficients. Specifically, the information is aggregated into the "low low" component of the decomposition. In one embodiment, kernels of the wavelet transform are selected so as to balance the computational efficiency of the transform with optimization of the aggregate information in the low pass components. This characteristic of wavelet transforms permits transfer, and subsequent display, of a good representation of the source image at a particular resolution while maintaining the computational efficiency of the transform.

The wavelet transform function embodiment generates mathematically independent information among the levels of the hierarchical representation. Accordingly, there is no redundant information in the pyramidal data structure 535. Thus, pyramidal data structure 535 is not merely multiple replications of the source image at different resolutions, which consists of redundant information, but it contains unique data at the different levels of the hierarchical representation. The mathematically independent nature of the wavelet transform permits minimizing the amount of data transferred over a network, by requiring only the transfer of "additional data" not yet transferred to the computer from the server necessary to construct a given image. The wavelet transforms are lossless, in that no data from the original source image is lost in the decomposition into the pyramidal data structure 535. Accordingly, the dynamic transfer syntax system has applications for use in medical imaging and medical imaging applications.

In one embodiment, fixed-point kernels are used in the wavelet transform (i.e., decomposition processing 525). The use of fixed-point kernels generates coefficients for the pyramidal data structure that permit an easy implementation into a standard pixel footprint. The wavelet transform, a spatial transform, generates a dynamic range of the "low low" component that is equal to the dynamic range of the source image. Because of this characteristic, the "low low" component does not contain overshoot or undershoot components. As a result, the use of fixed-point kernels is preferred because no normalization process to convert the transformed dynamic range to the pixel dynamic range is required.

For this embodiment, the dynamic image transfer system 500 directly utilizes the transform coefficients as pixels, without re-scaling the coefficients. The range of the high-pass components (i.e., "low high", "high low", and "high high" components) is the range of the input source data plus two bits per coefficient. This characteristic permits mapping of all components (i.e., high and low pass components) to a given pixel footprint.

The use of the wavelet transform to generate the pyramidal data structure provides a scalable solution for transferring different portions of a large data file. When the source image 515 is decomposed into the pyramidal data structure 535, sub-images and sub-resolution images are extracted directly from memory of the image server 100. The image server then transmits only the data, in the form of physical coefficients, required to reconstruct the exact size of the desired image for display at the client. Accordingly, the multi-resolution format is implicit in the pyramidal data structure.

A wavelet transform is a spatial transform. In general, in a spatial transform, the information is aggregated so as to preserve the predictability of the geometry of the source image. For example, using a wavelet transform with fixed point kernels, specific coefficients of the transform data may be identified that contribute to specific geometric features of the source image (i.e., a predefined portion of a source image is directly identifiable in the transform data). In another embodiment, the wavelet transforms use floating point kernels.

In other embodiments, the wavelet transform may be used to generate multi-spectral transform data. In general, multi-spectral transform data aggregates multi-components of the source image into a vector for the transform data. Through use of multi-spectral transform data, the wavelet transform may aggregate multi-dimensional data (e.g., two dimensional, three dimensional, etc.) for a source image. For example, multi-dimensional transform data may be used to reconstruct a source image in three dimensions. Also, the multi-spectral transform data may comprise any type of attribute for binding to the source image, such as color variations and/or non-visual components (e.g., infrared components).

In general, to generate the pyramidal data structure 535, the transform is applied across the columns, and then this transform, or a different transform, is applied across the rows. The selection of the transform for decomposition processing 525 is dependent upon the particular characteristics of the pyramidal data structure desired. Each level of the pyramidal data structure is generated by recurring on the low-pass, "low low", of the previous higher level. This recursion continues until a predetermined size is obtained. For example, in one embodiment, the lowest level in the pyramidal data structure for a source image having an aspect ratio of one-to-one consists of a low-pass component of 128×128. However, any granularity of resolution may be generated for use in a pyramidal data structure without deviating from the spirit or scope of the invention. Also, any quadrant may be used in the recursion process with any desired transform.

Figure 6A:
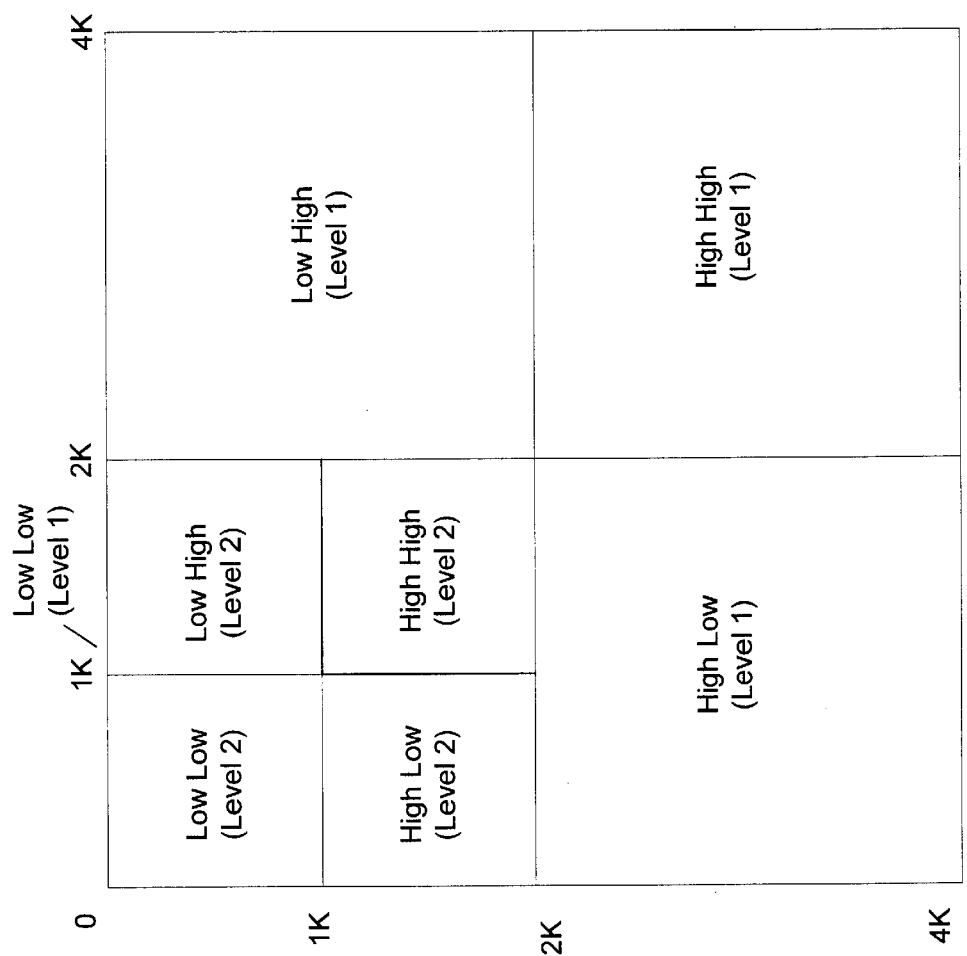
FIG. 6a illustrates an example of a pyramidal data structure.

FIG. 6a illustrates an example of a pyramidal data structure. For this example, the source image comprises a 4K×4K image. The decomposition processing 525 generates, in a first iteration, a level one Mallat structure. Specifically, as shown in FIG. 6a, a low-pass component, "low low", is generated and consists of a 2K×2K sub-image. The high-pass components, consisting of "low high", "high high", and "high low", contain physical coefficient coordinates (e.g., the upper right hand coordinate for the rectangle that constitutes the "low high" component is (4K, 0)).

Figure 6B:
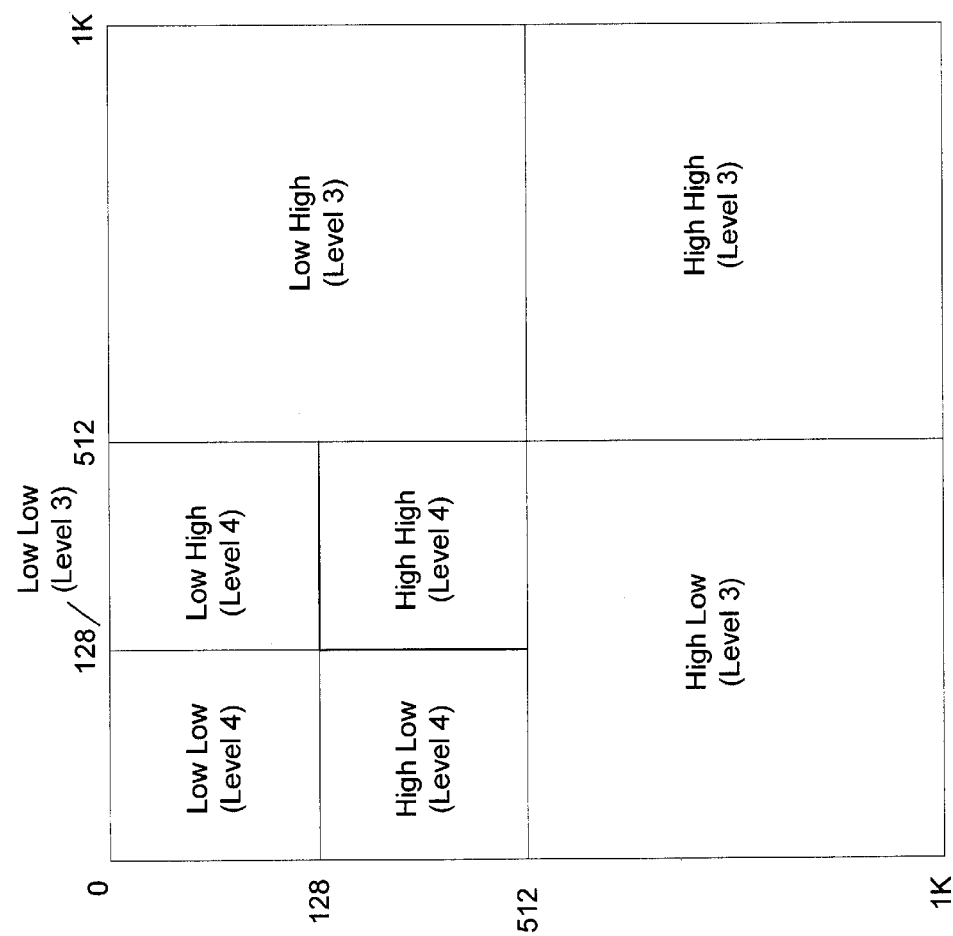

FIG. 6a also illustrates a second level decomposition. The second iteration of decomposition processing 525 operates on the low pass (i.e., "low low"), component of the level one data. For the second level, the low-pass component, "low low", consists of a 1K×1K sub-image, as labeled in FIG. 6a. FIG. 6b illustrates level three and level four decompositions for the 4K×4K source image of FIG. 6a. To generate the level three decomposition, decomposition processing 525 operates on the level two "low low" component (i.e., the 1K×1K image). For the level three transform, the low-pass component, "low low", is a 512×512 sub-image as labeled on FIG. 6a. FIG. 6b also illustrates a fourth level of decomposition for the 4K×4K source image. For the level four transform, the low-pass component comprises a sub-image of 256×256 pixels.

Any sub-band kernel or pyramid transform could be used within the infrastructure described by the dynamic image transfer; however, an integer kernel with no coefficient growth in the low pass term has particular advantages in that the low pass coefficients can be used without processing as pixels, and the transform can be inverted exactly in the integer domain. Although floating point kernels can have superior signal transfer characteristics, the additional processing required to use these coefficients as pixels, and the need for additional storage to guarantee perfect reconstruction works to their disadvantage.

The kernel consists of a low pass and a high pass biorthogonal filter. With input defined as $\{d_j\}$ and $[x]$ defined as the floor function, the forward transform is:

$$\text{Low}[j]=[(d_{2j}+d_{2j}+1)/2]$$

$$\text{High}[2]=d_{2j}-d_{2j+1}+\text{Poly}[j]$$

$$\text{Poly}[j]=[(3^*\text{Low}[j-2]-22^*\text{Low}[j-1]+22^*\text{Low}[j+1]-3^*\text{Low}[j+2]+32)/64]$$

The inverse transform, used to reconstruct the image, is:

$$d_{2j}=\text{Low}[j]+[(\text{High}[j]-\text{Poly}[j]+1)/2]$$

$$d_{2j+1}=\text{Low}[j]-[(\text{High}[j]-\text{Poly}[j])/2]$$

As discussed above, the wavelet transform is a spatial transform such that the information is aggregated to preserve the predictability of the geometry of the source image. Thus, coefficient coordinates, sufficient to reconstruct a desired image or sub-image at a particular level, are readily identifiable.

A more complete description of the dynamic transfer operation is contained in U.S. Provisional Patent Application, entitled "Flexible Representation and Interactive Image Data Delivery Protocol", Ser. No. 60/091,697, inventors Paul Joseph Chang and Carlos Bentancourt, filed Jul. 3, 1998, and U.S. patent application, entitled "Methods and Apparatus for Dynamic Transfer of Image Data", Ser. No. 09/339,077, inventors Paul Joseph Chang and Carlos Bentancourt, filed Jun. 23, 1999, both of which are expressly incorporated herein by reference.

Dynamic Image:

Once the user at the image recipient computer receives the first view of a source image, the user may desire to explore the source image by requesting different views. As discussed above, the different views may comprise different portions of the source image, as well as different resolutions of the source image. Thus, the user is not confined to viewing a single static view. Instead, the user receives a "dynamic image", such that the user may generate additional requests to see different views of the source image.

Figure 7A:
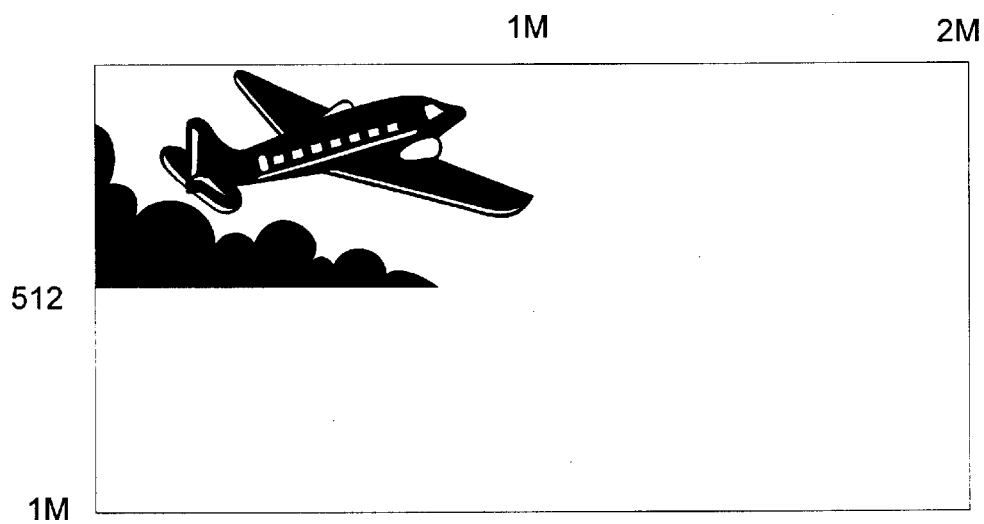
FIG. 7a illustrates a source image decomposed into a level one Mallat structure.
Figure 7B:
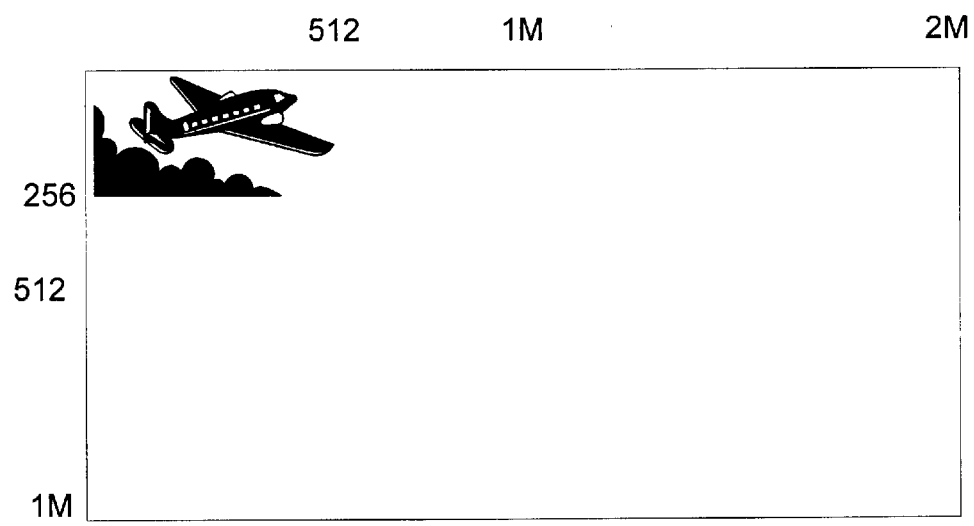
FIG. 7b illustrates a source image decomposed into a level two Mallat structure.

FIG. 7a illustrates a source image decomposed into a level one Mallat structure. For this example, the image sender may have an output display (i.e., computer monitor) capable of displaying the level one Mallat view of the source image (i.e., a computer monitor capable of displaying a 512×1 M pixel image). Also, for this example, the sender desires to send to a work associate a particular view in order to illustrate a particular point. To accomplish this task, the sender computer identifies the level one Mallat transform of the source image for display at 1 M×512. However, the image recipient computer may possess a computer monitor with a smaller resolution than the display resolution of the image sender computer. Thus, for this example, the image recipient computer cannot display the view of the source image identified by the image sender computer. Because the image is a dynamic image, the user at the image recipient computer may request a different view to accommodate the smaller resolution monitor at the recipient computer. Specifically, for this example, the image recipient computer requests transform data from the server sufficient to display the identified portion of the source image at a resolution of 512×256. The smaller resolution view is illustrated in FIG. 7b.

Dynamic Image Transfer System Applications:

The image transfer object of the present invention has application for use in maps and charts. For example, an image sender may transmit an image transfer object or an image identification to the recipient computer in order to provide directions to the image sender's physical address. The image identification may consist of a view of a particular street, showing the exact street location of the image sender. After seeing the view set forth in the image identification, the user of the image recipient computer may wish to obtain a better context for the exact street location by viewing a second image of the map that shows the nearest freeway or major streets. From the subsequent views, the image recipient may gain additional information necessary to fully navigate to the image sender's location. Thus, as illustrated by the above example, the image recipient may receive a specific view, as an initial starting point to convey information regarding the source image, and subsequently, through the dynamic image transfer process, obtain additional views of the source image as necessary.

The image transfer object of the present invention has application for use in medical imaging, teleradiology and medical informatics. It has become more common in the medical field for images to be stored, distributed, and viewed in digital form using computer technology. The image data (i.e., source images) are obtained by imaging equipment such as CT scanners or MRI scanners. The size of a data file for an image varies depending on the size and resolution of the image. For example, a typical image file for a diagnostic-quality chest X-ray is on the order of 10 megabytes (MB). The image data files are usually formatted in a "standard" or widely accepted format, such as the DICOM format. For the medical application, the source images 120 constitute digitized medical images or series generated from medical instrumentation (e.g., mammogram, X-Ray, MRI, CATSCAN, etc.). Using the image transfer object and the techniques described herein, medical images, and particular "views" of medical images, are distributed among medical professionals over networks. The medical imaging application provides a non-real time collaboration of medical images.

Although the present invention has been described in terms of specific exemplary embodiments, it will be appreciated that various modifications and alterations might be made by those skilled in the art without departing from the spirit and scope of the invention.

What is claimed is:

1. A method for communicating a plurality of views for a source image, said method comprising the steps of:
    transmitting, from an image sender computer to a recipient computer, a static reference to identify a source image on a server;
    generating, at said image recipient computer, a first request for a view of said source image to said server based on said static reference;
    transmitting data from said image server to said image recipient computer in response to said request;
    displaying said first view of said source image at said image recipient computer;
    receiving input from a user at said image recipient computer to select a second view of said source image;
    generating a second request to said image server for said second view;
    transmitting from said image server additional data to generate said second view of said source image; and
    displaying said second view of said source image at said image recipient computer.

2. The method as set forth in claim 1, wherein the step of transmitting a static reference comprises the step of transmitting said static reference object via e-mail.

3. The method as set forth in claim 1, wherein the step of transmitting a static reference comprises the steps of:
    coupling said image recipient computer to a web site; and
    receiving said static reference by downloading said static reference from said web site.

4. The method as set forth in claim 1, further comprising the steps of:
    receiving, at said recipient computer from said image sender computer, an image transfer object comprising methods and data, said data comprising said static reference;
    determining, from utilizing said image transfer object, if any additional software components are necessary to conduct dynamic image transfer;
    requesting, if additional software components are necessary, from a server said additional software components to conduct dynamic image transfer; and
    receiving at said image recipient computer said additional software components from said server.

5. The method as set forth in claim 1, further comprising the step of receiving, at a recipient computer from said image sender computer, an image transfer object comprising methods and data, said data comprising said static reference and said methods comprising functionality to conduct said dynamic image transfer.

6. The method as set forth in claim 1, wherein said source image comprises a medical image.

7. A method for communicating a plurality of views of a source image to recipient, said method comprising the steps of:
    storing, at an image server, transform data for at least one source image so as to permit construction of at least portions of said source image at different resolutions;
    transmitting, from an image sender to an image recipient, an identification of at least one view of said source image;
    generating, at said image recipient computer, a first request from said identification to said image server for transform data to reconstruct said view of said source image;
    transmitting said transform data requested from said image server to said image recipient computer;
    reconstructing said view of said source image at said recipient computer from said transform data; and
    displaying said view of said source image at said recipient computer.

8. The method as set forth in claim 7, wherein said source image comprises a medical image.

9. The method as set forth in claim 7, wherein the step of transmitting, from an image sender to an image recipient, an identification of at least a first view of said source image comprises the step of transmitting said identification via e-mail.

10. The method as set forth in claim 7, wherein the step of transmitting, from an image sender to an image recipient, an identification of at least a first view of said source image comprises the steps of:
    coupling said image recipient computer to a Web Site; and
    receiving said identification by downloading said image transfer object from said web site.

11. The method as set forth in claim 7, further comprising the steps of:
    receiving input from a user at said recipient computer to select a second view of said source image;
    generating a request to said image server for said second view;
    transmitting, from said image server additional data to generate said second view of said source image; and
    displaying said second view of said source image at said recipient computer based on said data.

12. A computer readable medium comprising a plurality of instructions, which when executed by a computer, causes the computer to perform the steps of:
    transmitting, from an image sender computer to a recipient computer, a static reference to identify a source image on a server;
    generating, at said image recipient computer, a first request for a view of said source image to said server based on said static reference;
    transmitting data from said image server to said image recipient computer in response to said request;
    displaying said first view of said source image at said image recipient computer;
    receiving input from a user at said image recipient computer to select a second view of said source image;
    generating a second request to said image server for said second view;
    transmitting from said image server additional data to generate said second view of said source image; and
    displaying said second view of said source image at said image recipient computer.

13. The computer readable medium as set forth in claim 12, wherein the step of transmitting a static reference comprises the step of transmitting said static reference object via e-mail.

14. The computer readable medium as set forth in claim 12, wherein the step of transmitting a static reference comprises the steps of:

coupling said image recipient computer to a web site; and receiving said static reference by downloading said static reference from said web site.

15. The computer readable medium as set forth in claim 12, further comprising the steps of:

receiving, at said recipient computer from said image sender computer, an image transfer object comprising methods and data, said data comprising said static reference;

determining, from utilizing said image transfer object, if any additional software components are necessary to conduct dynamic image transfer;

requesting, if additional software components are necessary, from a server said additional software components to conduct dynamic image transfer; and receiving at said image recipient computer said additional software components from said server.

16. The computer readable medium as set forth in claim 12, further comprising the step of receiving, at a recipient computer from said image sender computer, an image transfer object comprising methods and data, said data comprising said static reference and said methods comprising functionality to conduct said dynamic image transfer.

17. The computer readable medium as set forth in claim 12, wherein said source image comprises a medical image.

18. A system comprising:

at least one recipient computer for receiving a static reference from an image sender computer to identify a source image and for generating a first request for a view of said source image based on said static reference;

an image server, coupled to said recipient computer, for storing said source image, for receiving said first request, and for transmitting said data to said image recipient computer in response to said request;

wherein, said recipient computer for displaying said first view of said source image, for receiving input from a user to select a second view of said source image, for generating a second request to said image server for said second view;

wherein, said image server for transmitting additional data to said recipient computer to generate said second view of said source image; and wherein, said recipient computer for displaying said second view of said source image.

19. The system as set forth in claim 18, wherein said source image comprises a medical image.

* * * * *